United States Patent [19]

Pusatcioglu et al.

[11] Patent Number: 5,036,704
[45] Date of Patent: Aug. 6, 1991

[54] MOISTURE SENSOR

[75] Inventors: Selami Y. Pusatcioglu, Milwaukee; Joseph C. Zuercher, Brookfield; Edward G. Lewis, Mequon, all of Wis.

[73] Assignee: Gas Research Institute, Chicago, Ill.

[21] Appl. No.: 498,306

[22] Filed: Mar. 23, 1990

[51] Int. Cl.$^5$ .............................................. G01W 1/00
[52] U.S. Cl. .................................. 73/336.5; 73/29.05; 338/34
[58] Field of Search ..................... 73/336.5, 29.05; 338/34, 35

[56] References Cited

U.S. PATENT DOCUMENTS

| 4,083,765 | 4/1978 | Lawson | 204/195 |
|---|---|---|---|
| 4,514,278 | 4/1985 | Stephens et al. | 204/430 |
| 4,528,078 | 7/1985 | Hirschfeld | 204/129 |
| 4,549,134 | 10/1985 | Weiss . | |
| 4,562,725 | 1/1986 | Oka et al. | 73/336.5 X |
| 4,604,182 | 8/1986 | Seago | 204/403 |
| 4,612,019 | 9/1986 | Langhorst | 55/16 |
| 4,662,220 | 5/1987 | Laue | 73/336.5 |
| 4,681,855 | 7/1987 | Huang | 436/39 |
| 4,693,953 | 9/1987 | Torikai | 430/165 |
| 4,717,403 | 1/1988 | Choksi | 55/429 |
| 4,799,374 | 1/1989 | Bossart et al. | 73/1 G |
| 4,806,315 | 2/1989 | Diagle | 472/89 |
| 4,812,221 | 3/1989 | Madou et al. | 204/412 |
| 4,827,778 | 5/1989 | Bossart et al. | 73/863.21 |
| 4,954,238 | 9/1990 | Kato et al. | 73/336.5 X |

OTHER PUBLICATIONS

NASA Tech. Brief vol. 8, No. 2 Item 139, Nov. 1984—Trace Level Solid Polymer Electrolyte Hygrometic.
NASA Tech. Brief vol. 3, No. 1, Item 52, Jun. 1978, Long Lasting Solid-Polymer Electrolytic Hygrometer.

Primary Examiner—Hezron E. Williams
Assistant Examiner—Joseph W. Roskos
Attorney, Agent, or Firm—A. E. Chrow

[57] ABSTRACT

A moisture sensor (100) is provided that utilizes a sulfonated fluorocarbon film (10) having a thickness of less than about one micron and capable of providing accurate measurements of humidity and extremely fast response to change in humidity. A preferred embodiment of an electrical system (150) is disclosed for use with sensor (100) and a sulfonated tetrafluoroethylene perfluoroether copolymer form of the film is especially preferred.

7 Claims, 5 Drawing Sheets

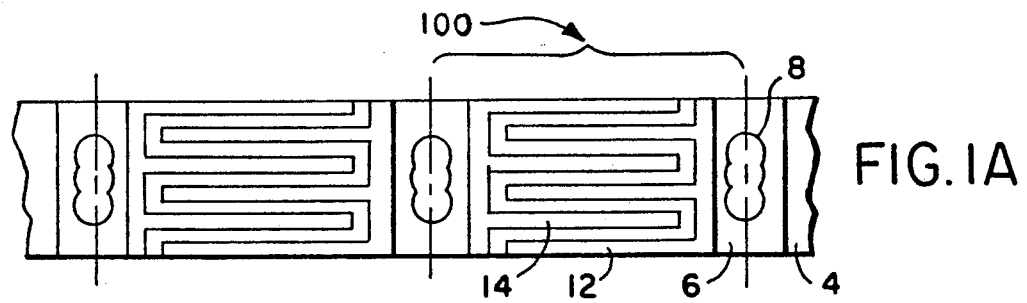
FIG. 1A
FIG. 1B
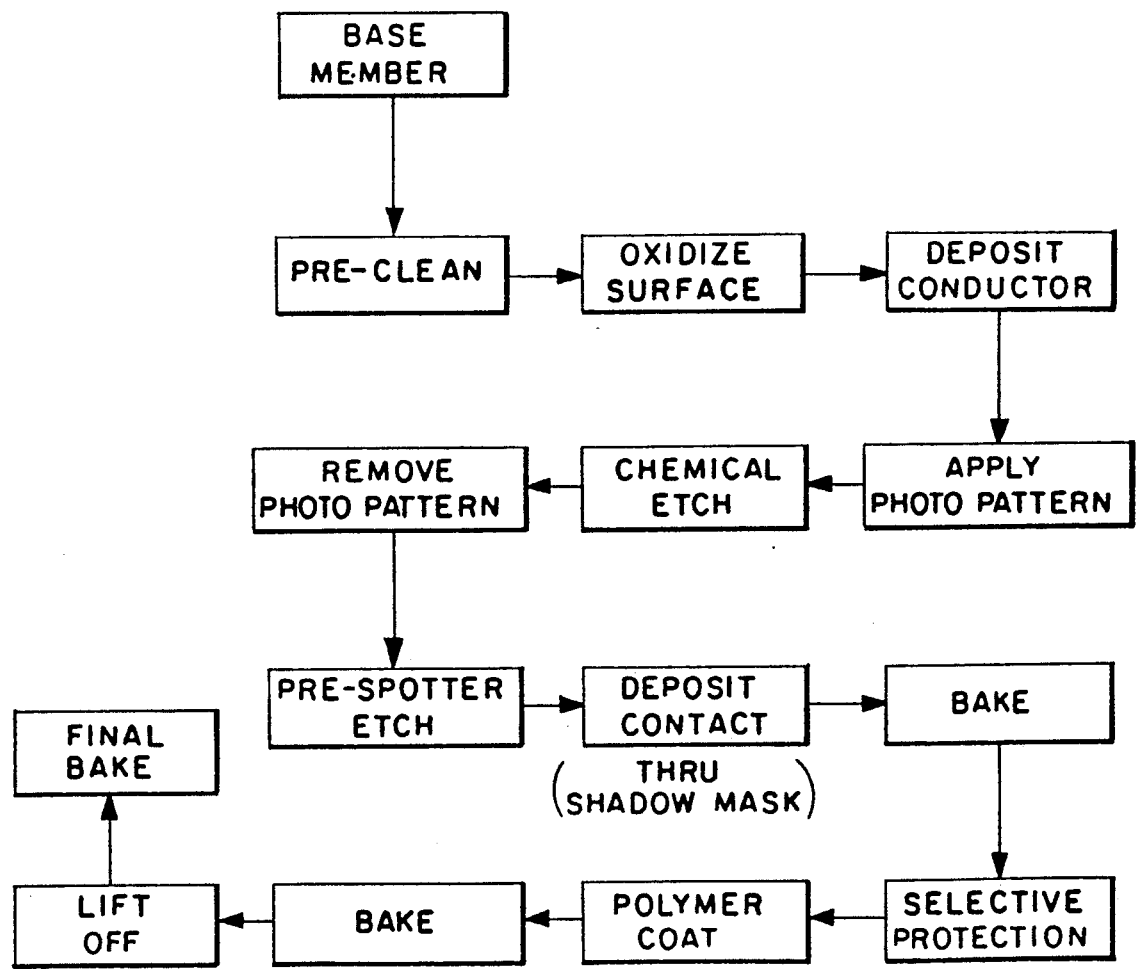
FIG. 2

NOTE: 1ST DATA AT 75%, 2ND DATA AT 32%, REMAINING DATA POINTS 96%

MOISTURE SENSOR

INTRODUCTION

This invention relates generally to a moisture sensor that utilizes a polymeric film having the ability to vary an electrical signal according to water content and more particularly to a low cost and accurate moisture sensor that utilizes a sulfonated fluorocarbon film having a thickness of less than about one micron to provide a fast response time in changing an electrical signal in response to changes in water content of the film as well as to a method for making the water sensor and to a system utilizing same.

BACKGROUND OF THE INVENTION

A variety of polymeric materials are known and have been employed in moisture sensors in past years that have the ability to vary an electrical signal in response to changes in their moisture content. Such materials include cellulose acetate butyrate and certain other cellulose based polymers, poly (styrene-sulfonic acid)—sodium form polymers, poly acrylamide, poly acrylate, and poly vinyl pyrollidone.

The present invention however utilizes sulfonated fluorocarbon polymer and more preferably a sulfonated tetrafluoroethylene perfluoroether copolymer in thin film form to provide a moisture sensor capable of operating over a broad temperature range with exceptionally fast response time to changes in water content.

Sulfonated fluorocarbon polymers and copolymers suitable for this invention are sold commercially by the Dupont Company under the trademark "NAFION".

Sulfonated Fluorocarbon polymers have been used to advantage in hygrometric applications in the past, but not in the manner of the present invention. An early example of the use of sulfonated fluorocarbon polymers in tube form for measuring water content of a gas is disclosed in National Aeronautics and Space Administration Technical Brief, Vol. 3, No. 1, item #52 (June 1978) and in strip form in Vol. 8, No. 2, Item #139 (November 1984) for measuring trace amounts of water in space and the former of which is also disclosed in U.S. Pat. No. 4,514,278 and the latter of which is also disclosed in U.S. Pat.No. 4,514,278, the disclosures of both of which are incorporated herein by reference.

Other examples of the use of sulfonated fluorocarbon Polymers in tubing form in hygrometric applications are disclosed in U.S. Pat. No. 4,604,182; 4,612,019; 4,717,403; and 4,799,374, the disclosures of all of which are incorporated herein by reference.

Examples of the use of sulfonated fluorocarbons in the form of a membrane that is generally thinner than sheet and much thicker than film is disclosed in U.S. Pat. No. 4,549,134 in which the membrane has a thickness of ½ to 2.5 mil and in U.S. Pat. No. 4,693,953 where the membrane has a thickness of 178 μm and in U.S. Pat. No. 4,528,078 where the membrane has a thickness of 170-180 μm and in U.S. Pat. No. 4,681,855 where the fluorocarbon includes certain other pendent groups in combination with sulfonic pendent groups and the membrane has a thickness of 0.1 mm.

It has been discovered however that attractively accurate and fast response time to changes in moisture level can be achieved by use of extremely thin sulfonated fluorocarbon film having a thickness of less than about one micron and which characteristically cannot be handled like a membrane, sheet or tubing and must be coated on to an appropriate support substrate preferably by spin coating or drawing through a layer of the material floating on the surface of water by a process that is commonly known in the art as the "Langmuir/Blodgett" film technique.

Also discovered is a simple and economical way of making a moisture sensor utilizing a film of sulfonated fluorocarbon having a thickness of less than about one micron in addition to providing a system that is operative to process the electrical output signal of the moisture sensor in a highly effective manner and preferably deliver it to a display or the like for visual monitoring of moisture content, or electronics data acquisition.

SUMMARY OF THE INVENTION

Accordingly, it is an object of this invention to provide a moisture sensor utilizing a sulfonated fluorocarbon film having a thickness of less than about one micron and characterized by having attractively fast response time to changes in humidity or water content.

It is another object of this invention to provide a unique and economical method for making a moisture sensor utilizing a sulfonated fluorocarbon film having a thickness of less than about one micron.

It is still a further object of this invention to provide a moisture measuring system that is highly effective in processing variations in an electrical signal provided by a moisture sensor utilizing a sulfonated fluorocarbon film having a thickness less than about one micron.

BRIEF DESCRIPTION OF THE DRAWINGS

FIGS. 1A and 1B are respective top and side views of a preferred embodiment of a moisture sensor 100 of the invention;

FIG. 2 is a block diagram of a preferred embodiment of a method of making moisture sensor 100 of FIGS. 1A and 1B;

DESCRIPTION OF SOME PREFERRED EMBODIMENTS

Figure 3:
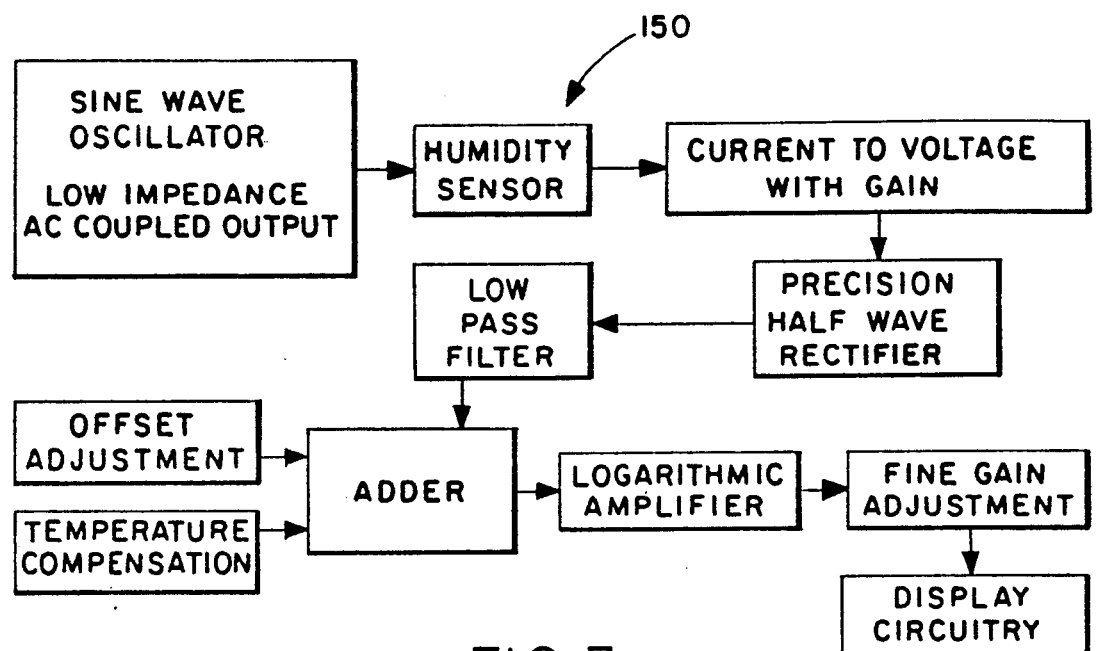
FIG. 3 is a block diagram of a preferred system 150 employing a moisture sensor made in accordance with the invention.

FIGS. 1A and 1B illustrate that a plurality of moisture sensors 100 can be made at one time such as where base member 2 is a layer made from a non-conductive or semi-conductive material such as quartz or silicon and more preferably where it is a wafer such as a p-type silicon wafer having a thickness of about 375 microns. Base member 2 is made from an insulator or an oxidizable material that when oxidized results in an insulator layer 4 which, when base member 2 is silicon, is silicon oxide having a thickness of preferably from about 1.0 to about 1.5 micron.

An electrical conductor 6 is deposited on layer 4 and then etched, as herein after described, to provide interdigital fingers of which two are referenced by numerals 12 and 14 in FIG.1A. Conductor layer 6 is preferably made from a highly conductive metal such as chrome and preferably has a thickness of about 0.15 to about 0.25 microns.

A moisture sensitive polymer coating 10 is deposited over the interdigital fingers of conductor layer 6 such that the coating 10 both covers and extends therebetween.

Polymer layer 10 is a thin layer havinq a thickness of less than about one micron and is deposited upon conductor layer 6 preferably by either spin coating as hereinafter described or by the well known Langmuir/Blodgett Technique where the substrate to be coated is drawn through a one molecule thick film of the polymer floating on water.

The vertical dashed lines in FIG. 1A illustrate how the plurality of moisture sensors can be cut to provide the individual sensors 100 described above.

Polymer film 10 is a sulfonated fluorocarbon film such as sold under the "NAFION" trademark by the Dupont Company as previously described. Preferably film 10 is made from a sulfonated fluorocarbon having only sulfonic pendant groups and even more preferably film 10 is made from a sulfonated tetrafluoroethylene perfluoroether copolymer having only sulfonic pendant groups sold under the "NAFION" trademark by the Dupont Company.

A preferred method of making moisture sensor 100 is shown in FIG. 2 where a surface base member (2), such as the silicon wafer previously described, is first precleaned and then oxidized such as by exposing the surface to steam at a temperature of about 1100° C. for about four hours to provide a silicon oxide layer 4 having a thickness of about from about 0.5 to about 1.5 micron and preferably about 1.1 micron which is equivalent to 11000 angstroms.

Next a layer of a highly electrically conductive material such as chrome is deposited onto layer 4 preferably by sputtering to provide conductor layer 6 having a thickness of from about 0.15 to about 0.25 microns and more preferably about 0.2 microns which is equivalent to 2000 angstroms.

Next a negative type resist photo pattern is laid over layer 6. The pattern is preferably in the form of interdigital fingers such as fingers 12 and 14 shown in FIG. 1A that are formed by chemically etching the exposed surfaces of layer 6 that are not masked by the resist.

The chemical etching is preferably accomplished by subjecting the exposed surfaces of layer 6 to transene chrome etchant for about 5-9 minutes followed by a one minute rinse with a 2% sulfuric acid solution that is then followed with a deionized water rinse.

The photoresist is then removed such as with oxygen plasma and the locations where contacts 8 are to be deposited are sputter etched such as by exposing it to a 150 watt argon arc for about five minutes.

Contacts 8, that are preferably made from gold as previously described, are then deposited onto conductor layer 6 through a shadow mask at the etched locations shown in FIG. 1A. Contacts 8 are preferably sputter deposited onto the etched locations of layer 6 by means of a 500 watt argon arc for about thirty minutes to provide a contact height of about 0.75 to about 1.5 microns or more preferably about 1 micron which is equivalent to 10,000 angstroms in thickness.

The product is then baked at a temperature of preferably about 70° C. for a time period of preferably about one hour in duration.

In preparation for polymer film 10, all surfaces not to be coated with the film are masked with a protective covering such as tape for which a thickness of about 50 microns has been found particularly advantageous.

Film or coating 10 is preferably applied to the unmasked surfaces by a spin coating process where a 5% alcohol and water solution of the sulfonated fluorocarbon polymer is dropped onto the unmasked surfaces and the entire wafer supported product is then rotated at about 1000 RPM for about sixty seconds to provide a coating thickness of less than about one micron and preferably about 0.5 microns which is equivalent to 5000 angstroms in thickness.

Finally, the masking tape is removed and the resultant product is then baked for about one hour at a temperature of preferably about 120° C. prior to cooling the product to ambient temperature and sending it for testing.

Figure 4:
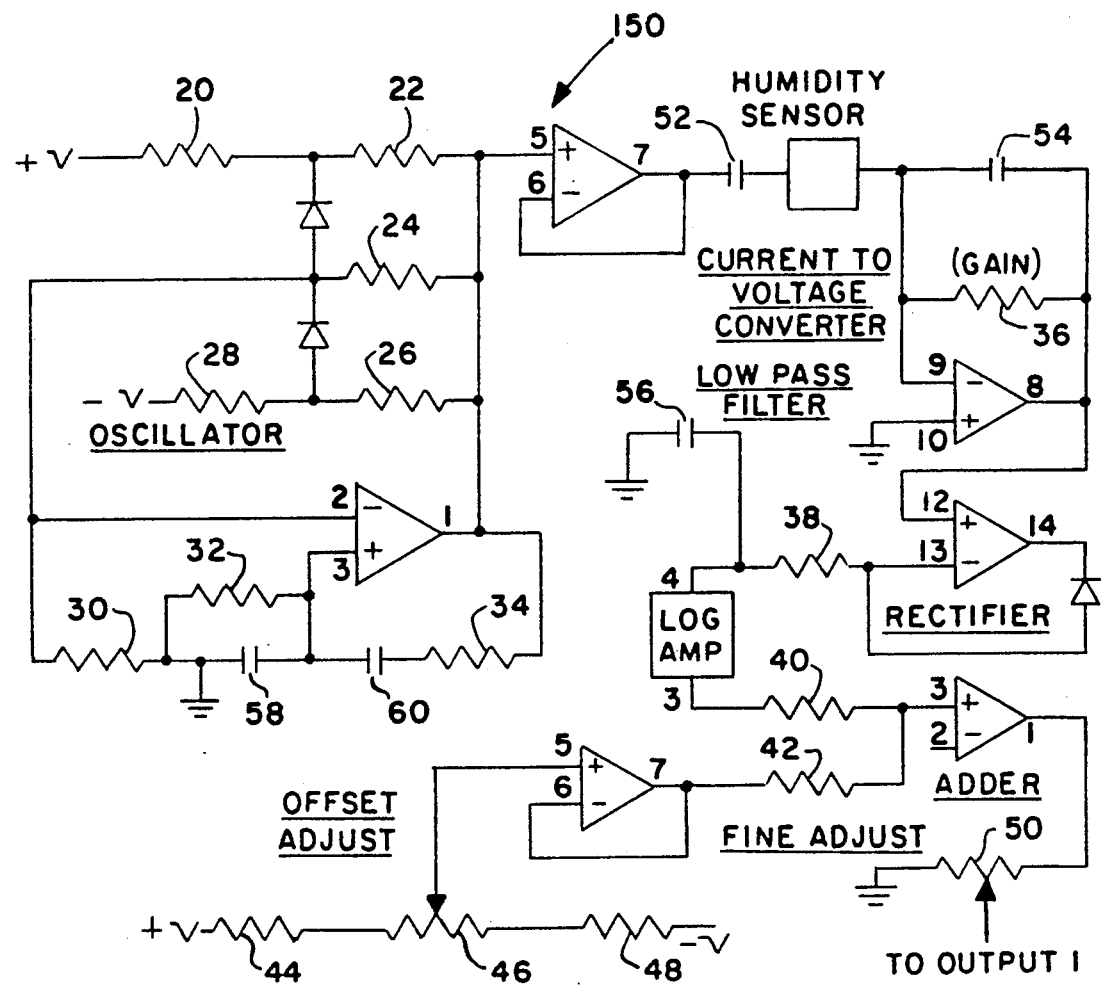
FIG. 4 is an electrical circuitry schematic diagram of the system of FIG. 3.

FIG. 3 shows a block diagram of a system 150 for which the electrical circuitry detail is shown in FIG. 4 and that has been found to be effective in processing an electrical output signal governed by the variation in electrical properties of film 10 of moisture sensor 100 in response to variations in humidity resulting in variations in moisture content of film 10.

The moisture sensor provides a varying electrical current output signal according to the moisture content of film 10 in response to an input voltage signal preferably provided by a low impedance alternating voltage coupled sine wave oscillator preferably operating at a frequency of about 1000 hertz.

The varying electrical current output is processed by first converting the current signal to a voltage signal preferably with gain so as to be able to magnify the resultant voltage signal.

The converted voltage signal is then delivered to a rectifier, preferably a precision half wave rectifier, afterwhich the rectified voltage signal is passed through a low pass filter to eliminate noise spikes and thence to an adder where it is adjusted for offset and temperature compensation prior to being delivered to an amplifier, preferably a logarithmic amplifier, after which it is adjusted with fine gain apparatus in preparation for being utilized in some manner such as by being delivered to optical displace circuitry.

The circuitry of FIG. 4 provides the system foundation hereinbefore described with respect to FIG. 3 and therefore will not be described in detail except for describing in TABLE I below the preferred values of resistance and capacitance referenced by numerals in FIG. 4.

TABLE I

| Numeral | Resistance (K. Ohms) |
| --- | --- |
| 20 | 20 |
| 22 | 330 |
| 24 | 21 |
| 26 | 330 |
| 28 | 20 |
| 30 | 10 |
| 32 | 10.5 |
| 34 | 10.5 |
| 36 | 20 |
| 38 | 500 |
| 40 | 24.9 |
| 42 | 24.9 |

TABLE I-continued

| Numeral | |
|---|---|
| 44 | 15 |
| 46 | 20 |
| 48 | 15 |
| Capacitance (in microfarads) | |
| 52 | 47 |
| 54 | .15 |
| 56 | 47 |
| 58 | .015 |
| 60 | .015 |

Figure 5:
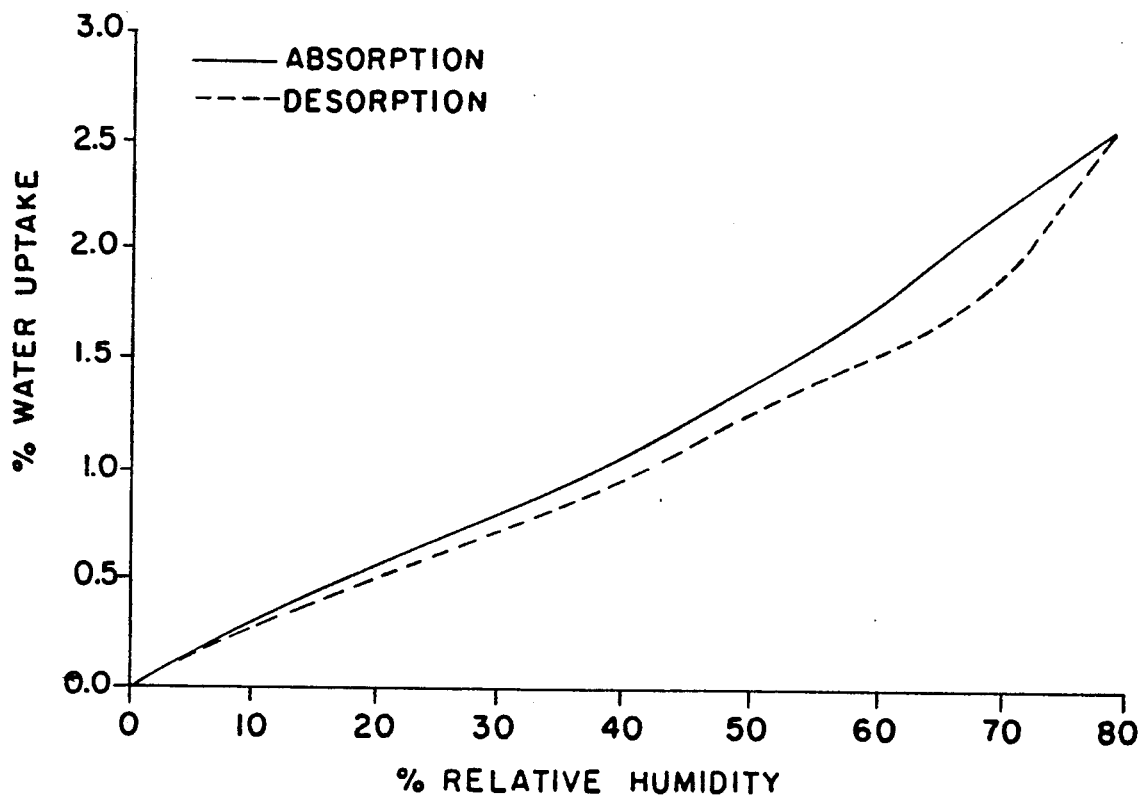
FIG. 5 is a graph showing water uptake of a sulfonated tetrafluoroethylene perfluoroether copolymer suitable for use in the moisture sensor of the invention.
Figure 6:
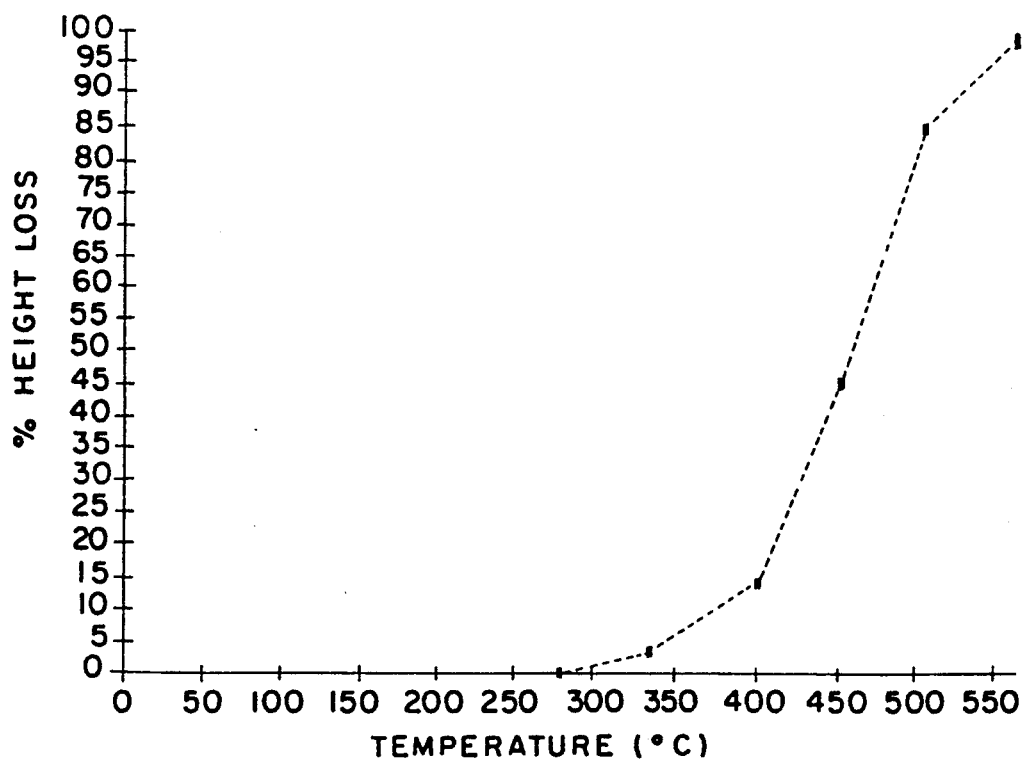
FIG. 6 is a thermogravimetric graph of the copolymer of FIG. 5.

FIG. 5 shows the excellent hysteresis characteristics of impedance magnitude of sulfonated tetrofluoroethylene perfluoroether copolymer where the water take up is virtually linear for increasing humidity and the curve (dashed) for desorption upon decreasing humidity is virtually the same as for the absorption or take up of water for increasing humidity. Such, when in the form of an extremely thin film of less than about one micron thick, provides high accuracy and repeatability and extremely fast response time. FIG. 6 is a graph showing that sulfonated tetrafluoroethylene perfluoroether copolymer exhibits no weight loss until a temperature of about 275° C. is reached which illustrates that a moisture sensor using the film would have attractively high temperature resistance.

Figure 7:
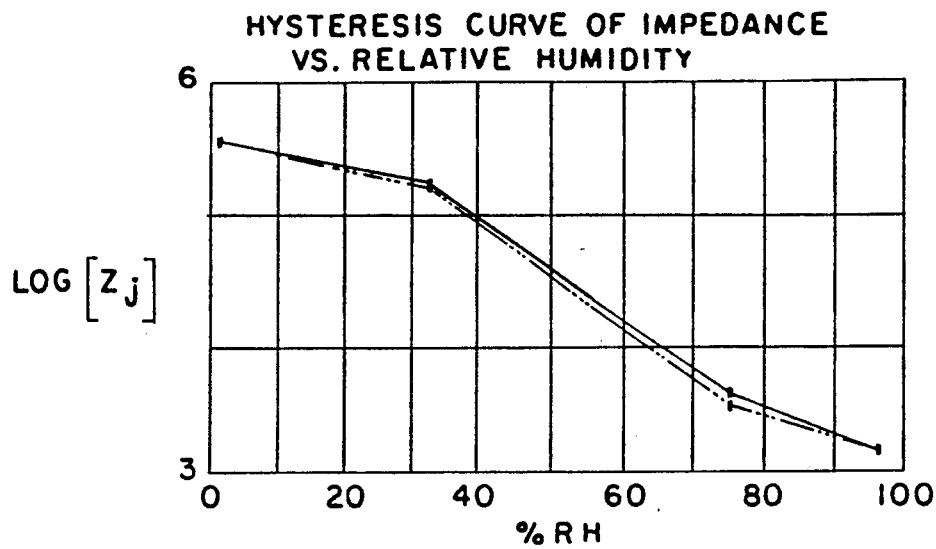
FIGS. 7-9 are three respective impedance performance graphs of moisture sensor 100.
Figure 8:
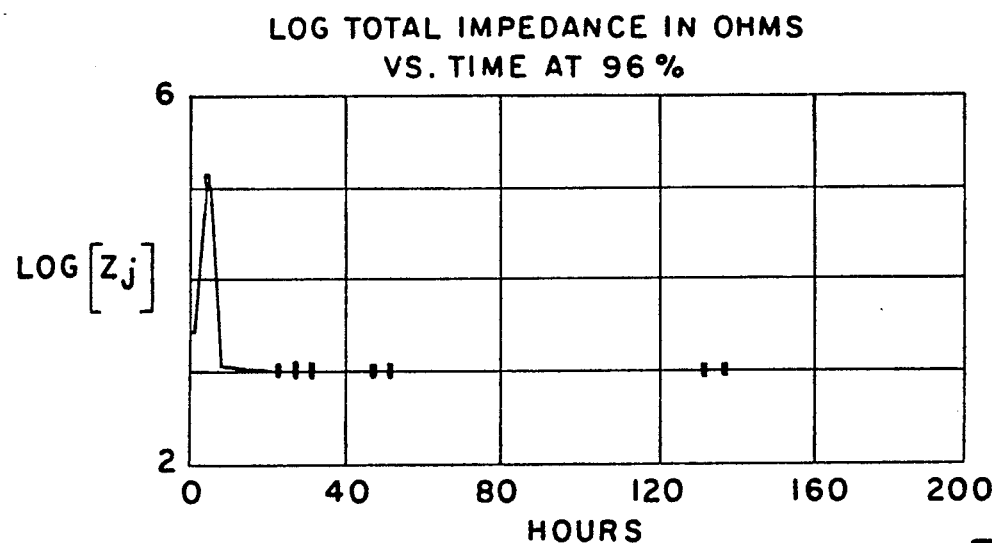
Figure 9:
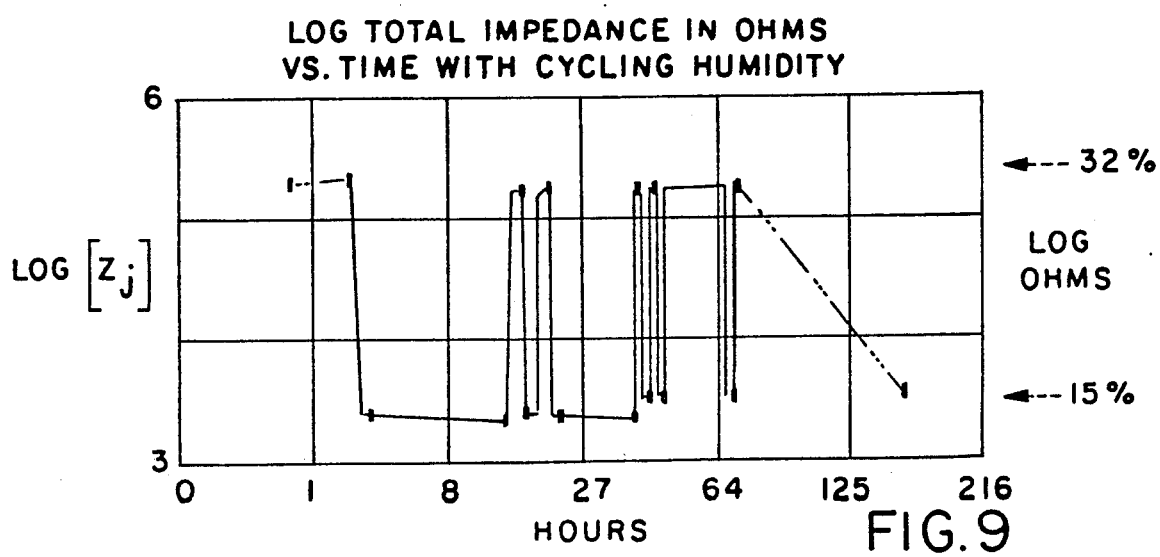

FIGS. 7-9 depict certain impedance performance characteristics of a moisture sensor made in accordance with the invention utilizing a film coating of about 0.5 micron of sulfonated tetrafluoroethylene perfluoroether copolymer.

The following described test values are associated with a moisture sensor made in accordance with the invention having the following approximate dimensions:

| | |
|---|---|
| Base member 2 thickness: | 375 microns |
| Oxide 4 layer thickness: | 1.1 microns |
| Chrome layer 6 thickness: | .2 micron |
| Chrome layer 6 width: | 1.6 microns |
| Gold contact 8 height: | 1.0 micron |
| Gold contact 8 width: | 2.0 mm. |
| Interdigital finger length: | 10.5 mm. |
| Interdigital finger width: | .04 mm. |
| Space between interdigital finger: | .045 mm. |
| Distance between interdigital finger sets: | 3.3 mm. |

FIG. 7 illustrates that the sensor has excellent hysteresis characteristics in that the impedance in ohms is close to linear between 0 and 100 percent relative humidity as well as being virtually the same whether the humidity is increasing or decreasing. FIG. 8 shows that the impedance in ohms of the above described sensor is virtually constant over long periods of time at a humidity of 96%.

FIG. 9 illustrates the repeatability of the sensor of the invention using an approximate 0.5 micron film of sulfonated tetrafloroethylene perfluoroether copolymer where the impedance in ohms returns to virtually the same value when cycling between 32% and 75% relative humidity over long periods of time.

Figure 10:
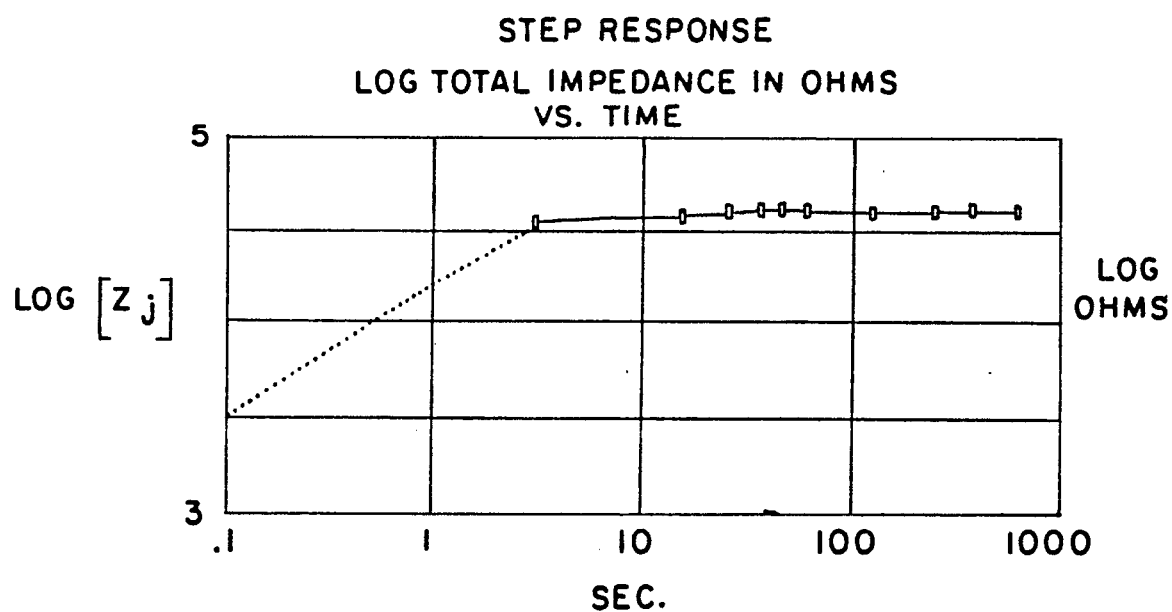
FIG. 10 is a graph showing change in electrical impedance of a sulfonated tetrafluoroethylene perfluoroether copolymer film of the invention in response to a change in humidity.

FIG. 10 clearly shows the very rapid response time on the order of less than 3 seconds in response to a step change in humidity from 75% to about 40%

Moisture sensors utilizing an extremely thin film of sulfonated fluorcarbon having a thickness of less than about one micron are reliable and accurate and exhibit high repeatability as well as being capable of operating over a broad temperature range (up to 250° C.) in addition to the fact that, in being a fluoronated polymer, the film is insoluble in water and is highly resistant to most chemicals including the characteristic of resisting swelling that would otherwise adversely affect the electrical characteristics.

A moisture sensor made in accordance with the invention utilizing an approximate 0.5 micron sulfonated tetrofluoroethylene perfluoroether film has been found to exhibit the characteristics shown in following TABLE II.

TABLE II

| PARAMETER | VALUE (typical) |
|---|---|
| Response from 75% to room humidity | 2-3 sec. |
| Drift at 96% relative humidity (330 hours) | −2% |
| Drift after condensation | .3% |
| 820 hr. drift (post testing) | .5% |
| Temperature Coefficient (%/°C.) | |
| at 32% relative humidity | 2.5%/°C. |
| at 75% relative humidity | 1.1%/°C. |
| Impedance | |
| (96% relative humidity) | 1.6K ohms |
| (1% relative humidity) | 320K ohms |
| Hysteresis (after full cycle) | 3% |
| Linearity of log total impedance | ±15% |
| Cycling 32-75% relative humidity 160 hrs. | 2.9% |

The above tests were conducted with an applied voltage of 0.25 volt at a frequency of 1000 hertz. The temperature, where applicable, was 24° C. and percent drift refers to change in log impedance relative to span.

A moisture sensor made in accordance with the invention has a response time found to be about one-third that of competitive polymeric resistive type moisture sensors and about 1/60 of polymeric capacitive type moisture sensors as well as exhibiting equivalent or superior characteristics in virtually every area investigated as well as being durable and economical to make.

What is claimed is:

1. A moisture sensor comprising a sulfonated tetrafluorethylene perfluoroether copolymer film having a thickness of less than about one micron, at least one pair of spaced-apart electrical conductors disposed in electrical contacting engagement with the film, and means for supporting the film and the electrodes, said film operative to affect an electrical input signal of predetermined type received through the conductors thereby and to provide an electrical output signal therefrom that varies according to the moisture content thereof.

2. A moisture sensing system comprising, a moisture sensor, said sensor comprising a sulfonated fluorocarbon film having a thickness or less than about one micron, at least one pair of spaced-apart electrical conductors disposed in electrical contacting engagement with the film, means for supporting the film and the conductors, said film operative to affect an electrical current input signal of predetermined type received through the conductors thereby and to provide an electrical current output signal, that varies according to the moisture content thereof, means for providing the electrical current input signal and means for processing the electrical current output signal to a condition effective to provide preselected electrical characteristics desired, said processing means including:

means for converting the output current signal to an electrical voltage signal, means for filtering the voltage signal to as to only pass a voltage signal that is below a predetermined value, and means for amplifying the passed voltage signal to a desired level.

3. The sensor of claim 2 wherein the electrical input signal is an electrical current input signal, the unprocessed electrical output signal is an processed electrical current output signal and the processing means includes; means for converting the output current signal to an electrical voltage signal, means for filtering the rectified voltage signal so as to only pass a voltage signal that is below a predetermined value, and means for amplifying the passed voltage signal to a desired level.

4. The system of claim 2 including means for displaying the amplified voltage signal.

5. The system of claim 2 wherein the electrical input signal is provided by an alternating electrical current sine wave oscillator at a predetermined frequency.

6. The system of claim 2 including means for compensating the filtered voltage signal for temperature.

7. The system of claim 2 to wherein the amplifier is a logarithmic amplifier.

* * * * *